(12) United States Patent
Bille

(10) Patent No.: US 8,920,690 B2
(45) Date of Patent: *Dec. 30, 2014

(54) SYSTEM FOR FORMING AND MODIFYING LENSES AND LENSES FORMED THEREBY

(71) Applicant: Perfect IP, LLC, Dallas, TX (US)

(72) Inventor: Josef F. Bille, Heidelberg (DE)

(73) Assignee: Perfect IP, LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/039,398

(22) Filed: Sep. 27, 2013

(65) Prior Publication Data

US 2014/0084501 A1    Mar. 27, 2014

Related U.S. Application Data

(62) Division of application No. 13/030,958, filed on Feb. 18, 2011, now Pat. No. 8,568,627, which is a division of application No. 12/717,886, filed on Mar. 4, 2010, now Pat. No. 8,292,952.

(60) Provisional application No. 61/209,362, filed on Mar. 4, 2009, provisional application No. 61/209,363, filed on Mar. 4, 2009, provisional application No. 61/181,420, filed on May 27, 2009, provisional application No. 61/181,519, filed on May 27, 2009, provisional application No. 61/181,525, filed on May 27, 2009.

(51) Int. Cl.
  *B29D 11/00* (2006.01)

(52) U.S. Cl.
  USPC ............................................. 264/1.37; 264/482

(58) Field of Classification Search
  USPC ........................... 264/1.37, 2.7, 400, 482, 1.1
  See application file for complete search history.

(56) References Cited

U.S. PATENT DOCUMENTS 8,568,627 B2 * 10/2013 Bille ............................ 264/1.37

* cited by examiner

*Primary Examiner* — Mathieu D. Vargot
(74) *Attorney, Agent, or Firm* — David W. Carstens; Jeffrey G. Degenfelder; Carstens & Cahoon, LLP

(57) ABSTRACT

A lens for placement in a human eye, such as intraocular lens, has at least some of its optical properties formed with a laser. The laser forms modified loci in the lens when the modified loci have a different refractive index than the refractive index of the material before modification. Different patterns of modified loci can provide selected dioptic power, toric adjustment, and/or aspheric adjustment provided. Preferably both the anterior and posterior surfaces of the lens are planar for ease of placement in the human eye.

27 Claims, 11 Drawing Sheets

SYSTEM FOR FORMING AND MODIFYING LENSES AND LENSES FORMED THEREBY

CROSS-REFERENCE

This application is a division of U.S. patent application Ser. No. 13/030,958 filed on Feb. 18, 2011, now U.S. Pat. No. 8,568,627, which in turn is a division of U.S. patent application Ser. No. 12/717,886 filed on Mar. 4, 2010 (now U.S. Pat. No. 8,292,952), which claims the benefit of provisional application Ser. Nos. 61/209,362 filed Mar. 4, 2009; 61/209,363 filed Mar. 4, 2009; 61/181,420 filed May 27, 2009; 61/181,519 filed May 27, 2009; and 61/181,525 filed May 27, 2009. These provisional applications are incorporated herein by this reference. To the extent the following description is inconsistent with the disclosures of the provisional applications, the following description controls.

BACKGROUND

Lenses are implanted in eyes to improve vision. In general there are two types of intraocular lenses. One type replaces the eye's natural lens, usually to replace a cataractous lens. The other type is used to supplement an existing lens and functions as a permanent corrective lens. Replacement type of lenses are implanted in the posterior chamber. A supplemental type of lens, referred to as a phakic IOL (intraocular lens), is implanted in the anterior or posterior chamber to correct refractive errors of the eye.

There are two common techniques used for forming intraocular lenses. One technique is molding, where an optical polymeric material is formed into a desired shape having a predetermined dioptic power. These lenses are available in standard diopter powers, typically differing in about 0.5 diopter power. A problem with the molding technique is it is a very expensive way to make a customized lens, and thus for most patients, only an approximate approach to clear vision is obtained. For some patients the diopter power can be wrong by 0.25 or more. Moreover, such lenses generally are not as effective for patients who have an abnormally shaped cornea, including some that have undergone a cornea procedure, such as LASIK surgery.

The other technique used is lathing and milling, where a disc shaped lens blank is ground to a desired shape. Due to the properties of the materials used for intraocular lenses, it is preferable to machine lenses at a reduced temperature such as −10° F. A problem with lathing and milling is that the optical properties of a lens at −10° F. may be different than the optical properties of the lens at body temperature, and thus such a lens only approximates optimal vision. In addition, as the lens warms it absorbs moisture and dimensions of the lens may change, thus altering the diopter power of the lens.

For some patients, it is desirable that the lenses be aspheric to correct corneal spherical aberrations or toric to correct or mitigate corneal astigmatism over a range of diopters. Commercially available IOLs generally cannot uniformly correct these optical defects because it would be necessary to inventory hundreds, if not thousands, of different types of lenses, all varying in dioptic power, and aspheric and toric features.

Another problem associated with conventional manufacturing techniques is that the lens often cannot accommodate the needs of patients that have undergone a LASIK (laser assisted in situ keratomileusis) surgery. LASIK surgery can correct for myopia, hyperopia, and/or astigmatism. However, alterations in the cornea created in the LASIK procedure make it very difficult to find an IOL with the appropriate adjustment for asphericity. A conventional IOL is generally not satisfactory for patients that have undergone a LASIK procedure or with an abnormal cornea, because of the challenge in inventorying IOLs suitable for such a patient.

A technique for modifying the refractive index of an optical polymeric material such as in an IOL is discussed in Knox et al., U.S. Publication No. 2008/0001320. This technique uses a laser for changing the refractive index of small areas of an optical material, resulting in changes in refractive index of up to about 0.06, which is an inadequate change in diopter power for most applications.

Accordingly, there is a need for a system for forming intraocular lenses that overcomes the disadvantages of prior art manufacturing techniques, and also allows for customization of lenses to provide multiple corrective features to approach optimum vision, including for patients that have had a LASIK procedure.

SUMMARY

The present invention provides a system that meets this need, and also provides lenses formed and modified by this system. A lens formed by this system has unique properties. The lenses typically are IOLs, but the invention has other applications, as discussed below. A lens according to this invention comprises a body formed of an optical material having a refractive index. The body has opposed interior and posterior surfaces, and an optical axis. The body contains modified loci. The modified loci have been formed by a laser beam and have a different refractive index than the material before modification. The lens has many unique features, and can be characterized by having at least one of the following features, all of the following features, or any combination of the following features:

(i) sufficient modified loci in the body so that the refractive index of the body has been modified sufficiently to change the diopter power of the body by at least plus or minus 0.5 (i.e., a positive diopter power change of at least 0.5 or a negative diopter power change of −0.5 or more such as −10;

(ii) at least some of the modified loci have an optical path length of from 0.1 to about 1 wave greater than the optical path length of a non-modified locus, wherein the wavelength is with respect to light of wavelength of 555 nm;

(iii) at least some of the modified loci are in a substantially circular pattern around the optical axis;

(iv) sufficient modified loci that at least 90% of light projected onto the anterior surface in a direction generally parallel to the optical axis passes through at least one modified locus;

(v) at least some of the modified loci are right cylindrical in shape with an axis substantially parallel to the optical axis and a height of at least 5 μm;

(vi) both the posterior and anterior surfaces are substantially planar; and (viii) each modified locus has a depth of from 5 to 50 μm.

Typically there are at least 1,000,000 or more modified loci located in a first layer of the body, the first layer being substantially parallel to the anterior surface, where the layer is about 50 μm thick. A circular pattern, referred to as an annular ring pattern, of modified loci can be used.

When the modified loci are used to obtain a desired optical effect, and more conventional constructions are not used, then preferably there are sufficient loci that at least 99% of the light projected onto the anterior surface of the body in a direction generally parallel to the optical axis passes through at least one modified loci. Thus substantially all optical effects provided by a lens can be provided by the modified loci.

The lens can provide a dioptic power adjustment, and can also be used for providing toric adjustment and/or aspheric adjustment.

An advantage of the present invention is the body of the lens can be made very thin, in the order from about 50 to about 400 μm maximum thickness, which allows for easy insertion into the posterior chamber of an eye in the case of an intraocular lens. This also allows a physician to make a smaller incision in the eye than is possible with installing conventional intraocular lenses. Preferably the maximum thickness of the body is about 250 μm.

An advantage of the version of the invention where both the anterior and posterior surfaces are substantially planar is there are no features on the body that can interfere with placement of an IOL in the posterior chamber of the eye.

Typically the modified loci have a depth of from about 5 to about 50 μm. Each modified loci can have from 1 to 10 sites, each site typically being formed by a sequence of about 100 infrared laser pulses in a single burst focused on a single spot, i.e., site. At least some of the modified loci can be contiguous to each other.

There can be multiple layers of modified loci, where each layer can have a thickness of about 50 μm. Typically the layers are spaced apart from each other by about 5 μm.

In the multiple layer version of a lens, at least some of the modified loci in the first layer can have an optical path length of at least 0.1 wavelength greater than the optical path length of a non-modified locus, where the wavelength with respect to the light of a first wavelength. The second layer can have modified loci having an optical path length of at least 0.1 wavelength greater than the optical path length of non-modified locus, with respect to the light of a second wavelength which differs from the first wavelength by at least 50 nm. There can also be a third layer, where the difference in optical path length is at least 0.1 wavelength with respect to a light of a third wavelength, where the third wavelength is at least 50 nm different than both the first and second wavelengths. For example, the first layer can be with respect to green light, the second layer with respect to red light, and the third layer with respect to blue light.

In the multiple layer version of the invention, the first layer can focus light at a first focal spot. The second layer can focus light at a second focal spot, spaced apart from the first focal spot, and additional layers can focus light at further additional spots.

Typically the material for the lens comprises a polymeric matrix. Optionally an absorber, preferably in an amount of at least 0.01% by weight of the material, can be used where the absorber is for light of the laser beam wavelength.

The system also includes apparatus for modifying the optical properties of a polymeric disc to form the lens. The apparatus can comprise a laser emitting a pulsed beam, a modulator for controlling the pulse rate of the beam, focusing lens for focusing the beam into a first region in the disc, and a scanner for distributing the focused beam into multiple loci in the region. There is also a holder for the lens, and means for moving the disc so that multiple regions of the disc can be modified. Preferably the modulator produces pulses between 50 and 100 MHz repetition rate. The pulse emitted by the laser can have a duration of from about 50 to about 100 femtoseconds and an energy level of about 0.2 nJ. The focusing lens can be a microscope objective that focuses to a spot size of less than 5 μm.

The scanner can be a raster scanner or a flying spot scanner, and in the case of a raster scanner, cover a field of view of about 500 μm.

The system also provides a method for forming these lenses. When forming a lens a disc formed of an optical material is held, and then modified loci are formed in the held disc with a laser beam.

The method can comprise the steps of emitting a pulsed beam from the laser, controlling the pulse rate of the beam with the modulator, focusing the beam in a first region in the lens, distributing the focused beam in multiple loci in the region, and moving the lens to modify loci in multiple regions of the disc.

The method and system can also be used for modifying the optical properties of a lens, such as an intraocular lens located in the posterior chamber or anterior chamber, contact lens, or natural lens. This can be affected by forming modified loci in the lens just as if they have been using the same procedure for forming a modifying lens that is used before the lens is implanted. One difference is that the lens in situ is not moved to modify different regions, but rather the focusing system of the apparatus is used to illuminate different regions of the in situ lens. During in situ processing, the eye of the patient can be stabilized according to conventional techniques used during ophthalmic surgery.

DRAWINGS

These and other features, aspects, and advantages of the present invention will become better understood with regard to the following description, appended claims, and accompanying drawings where:

Figure 2:
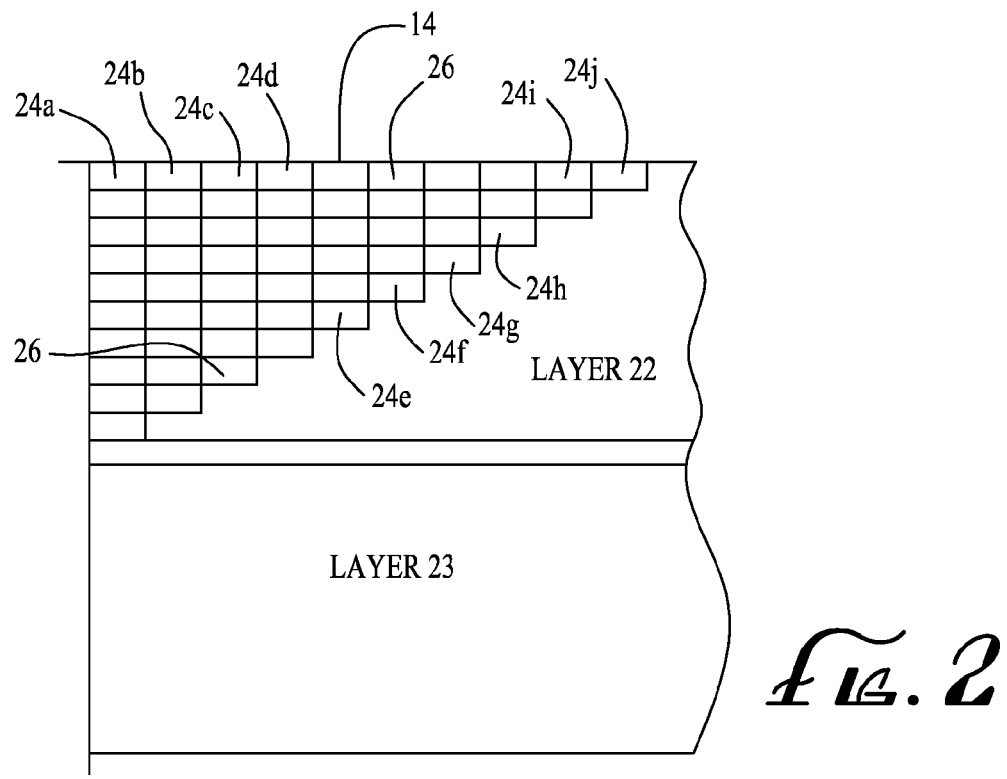
Figure 3:
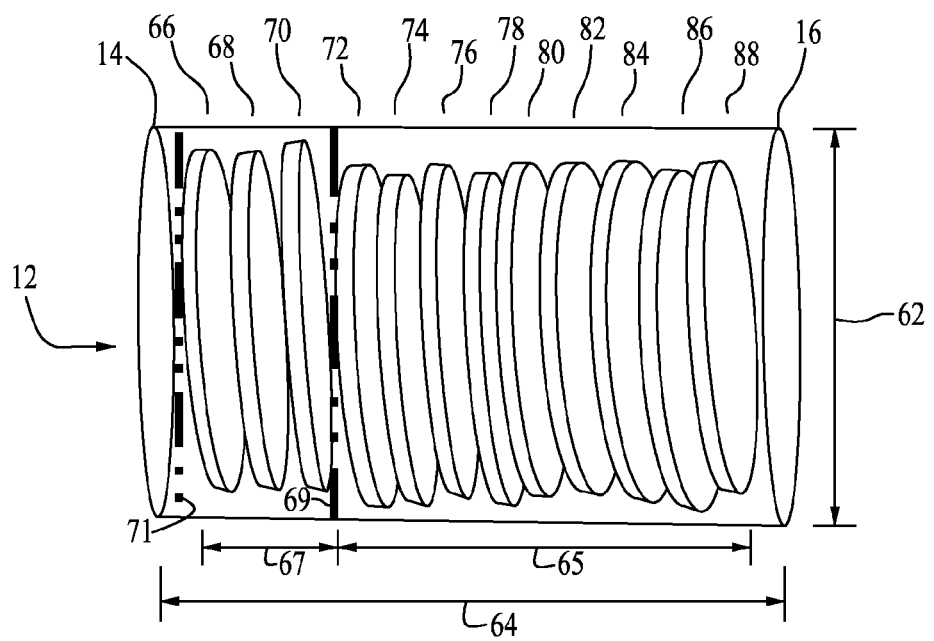
Figure 4A:
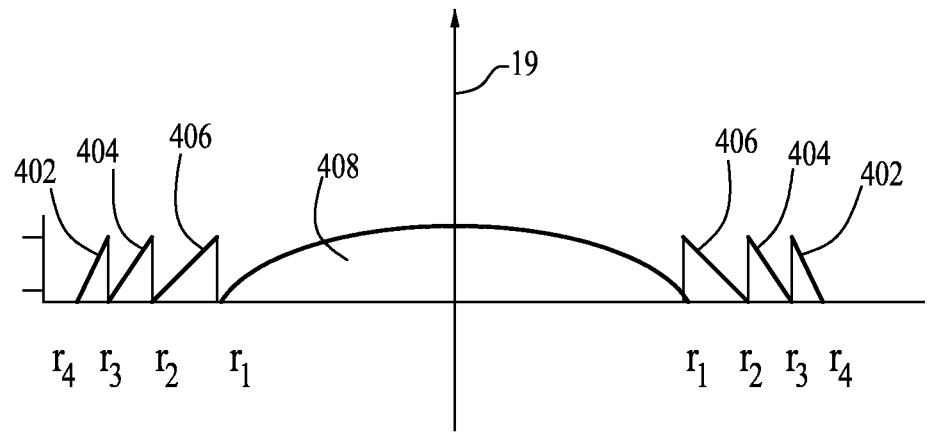
Figure 4B:
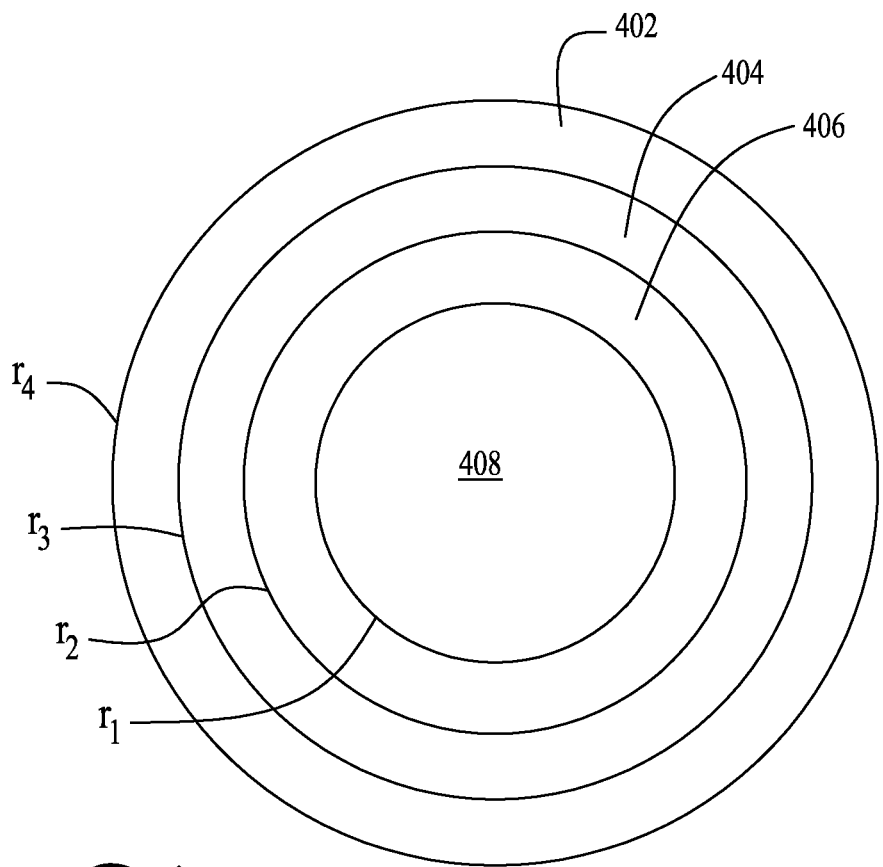
Figure 4C:
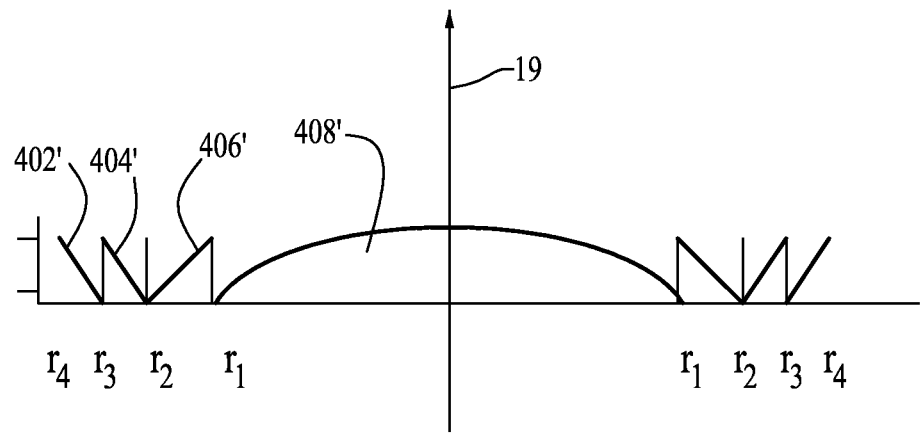
Figure 4D:
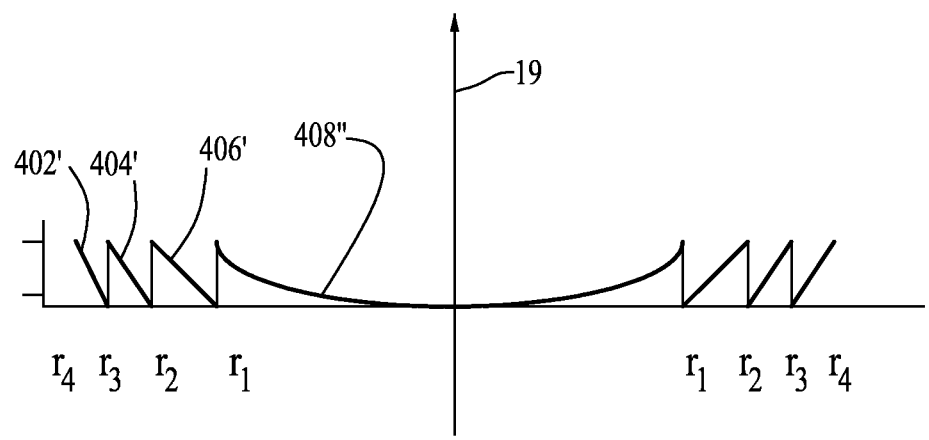
Figure 4E:
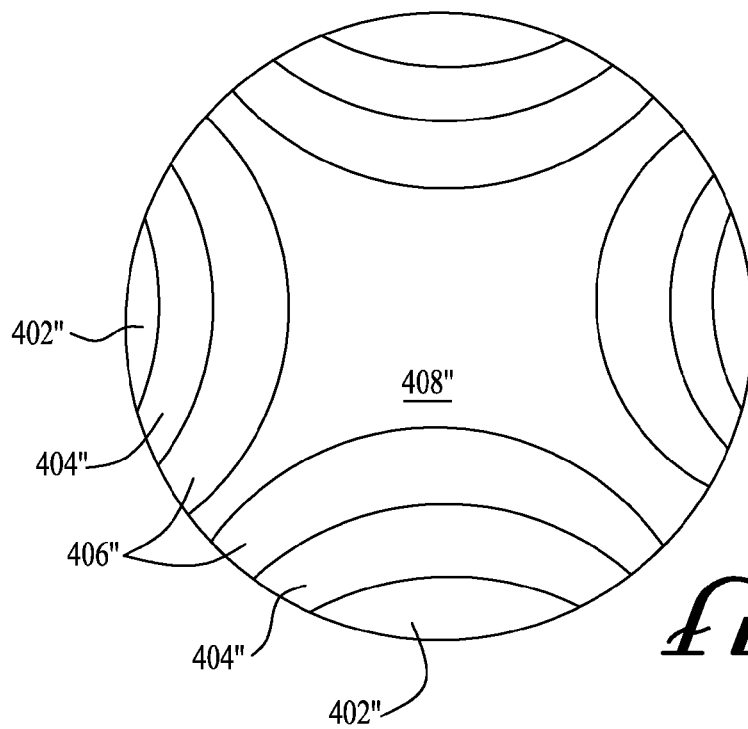
Figure 5:
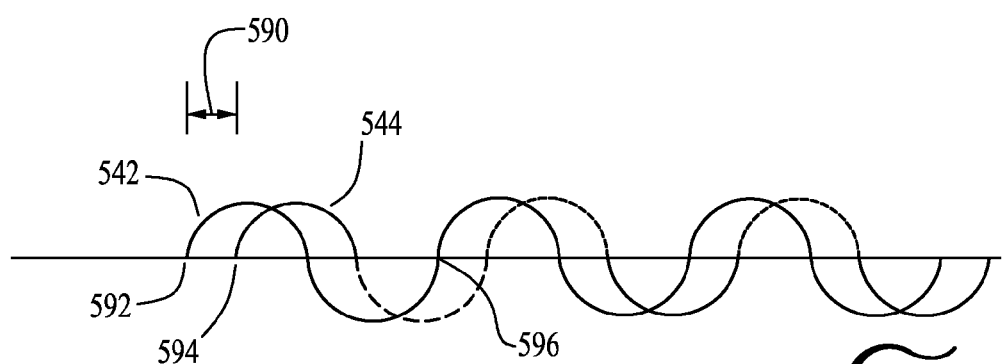
Figure 6:
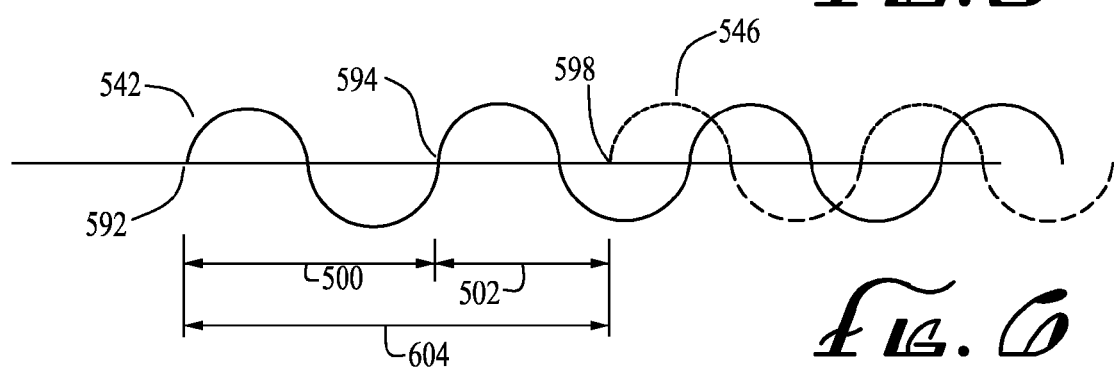
Figure 7:
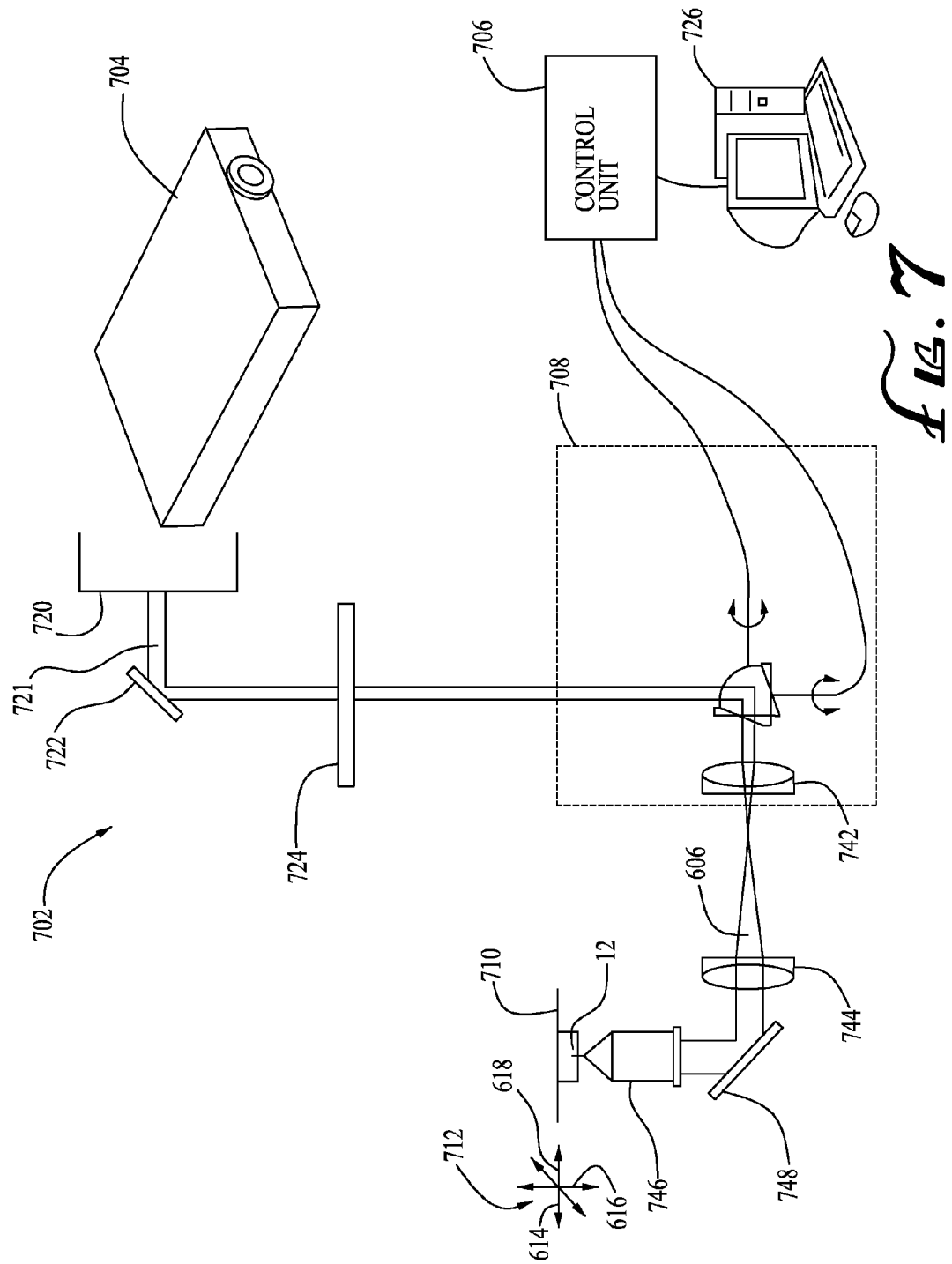
Figure 8:
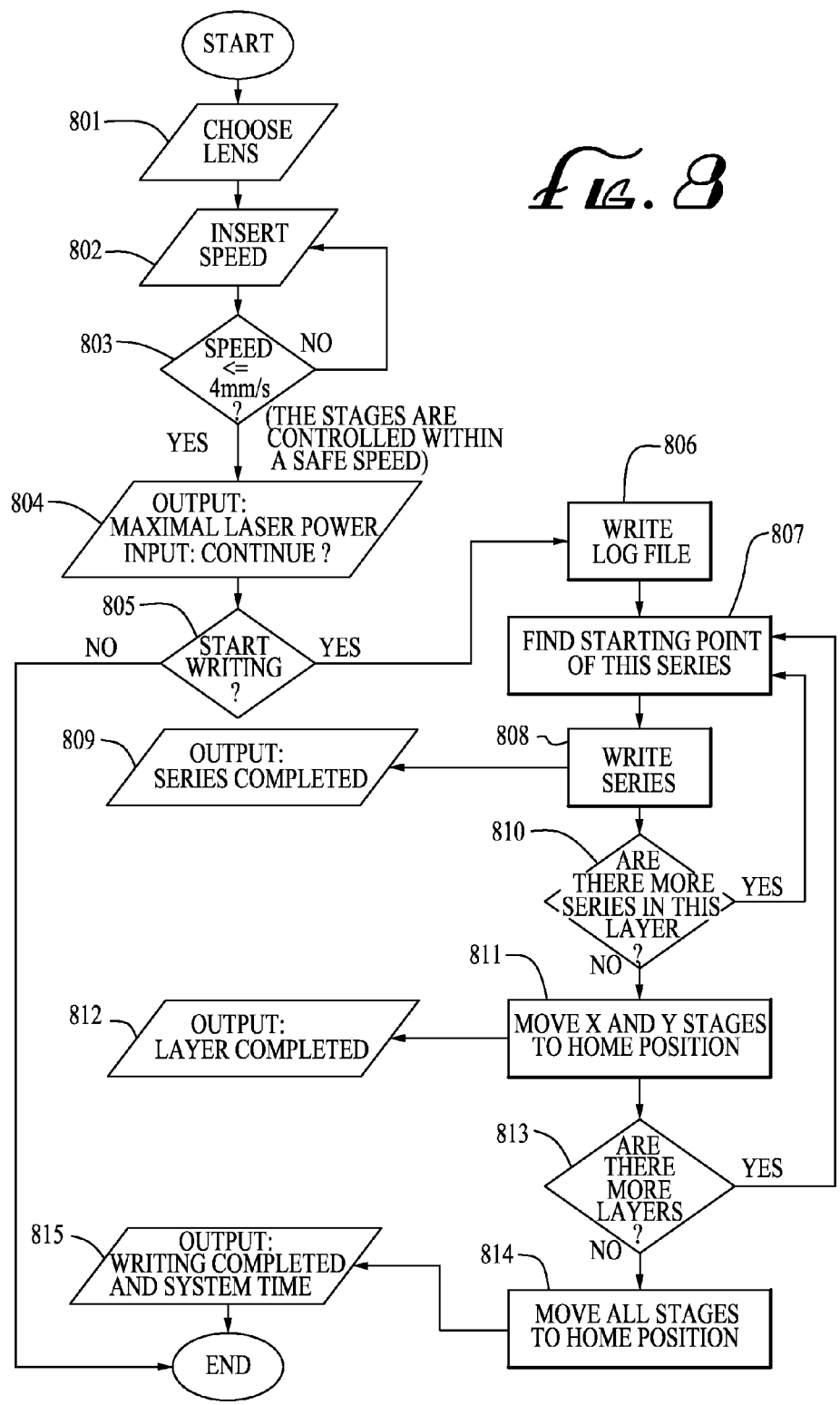
Figure 9:
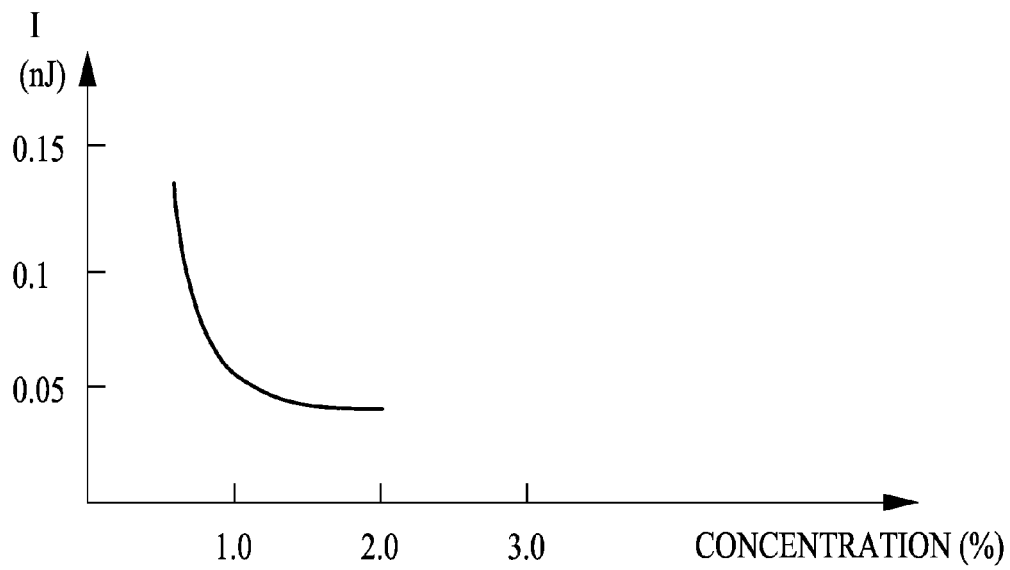
Figure 10A:
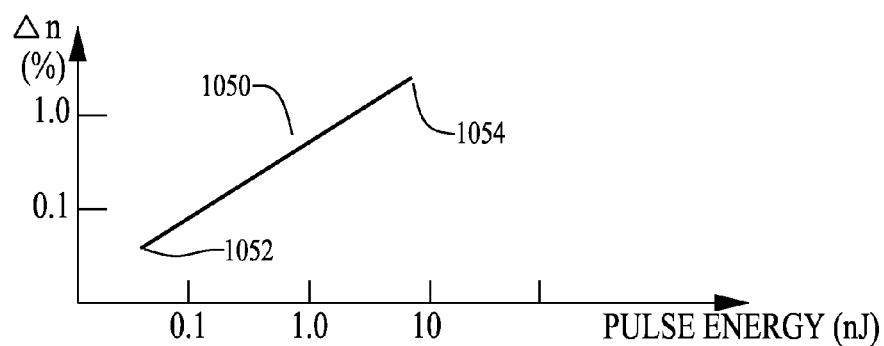
Figure 10B:
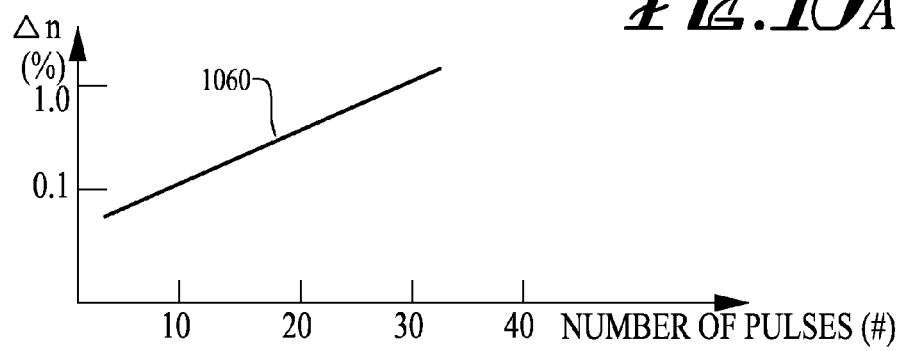
Figure 11:
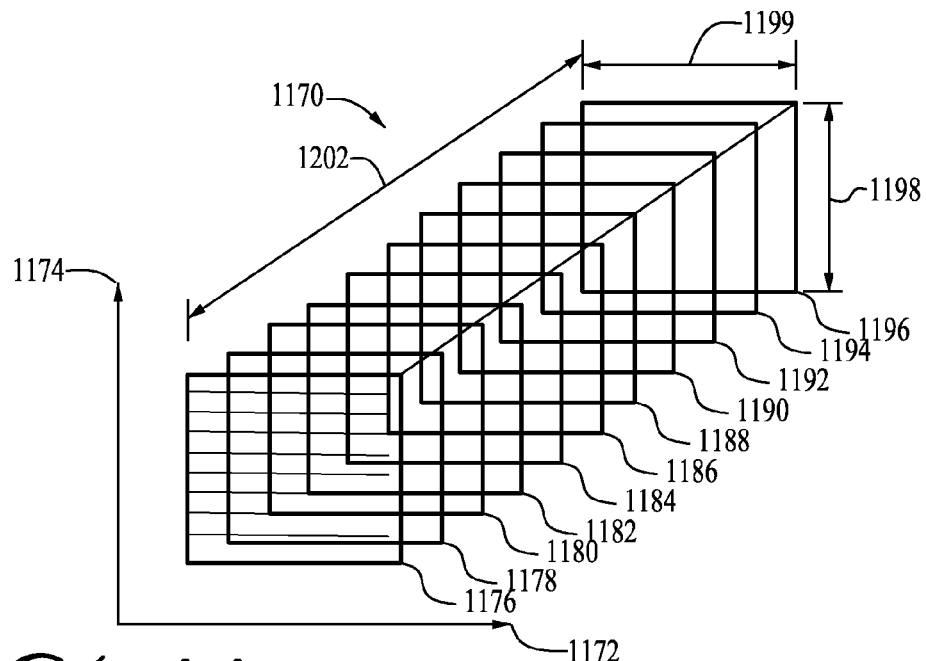
Figure 12:
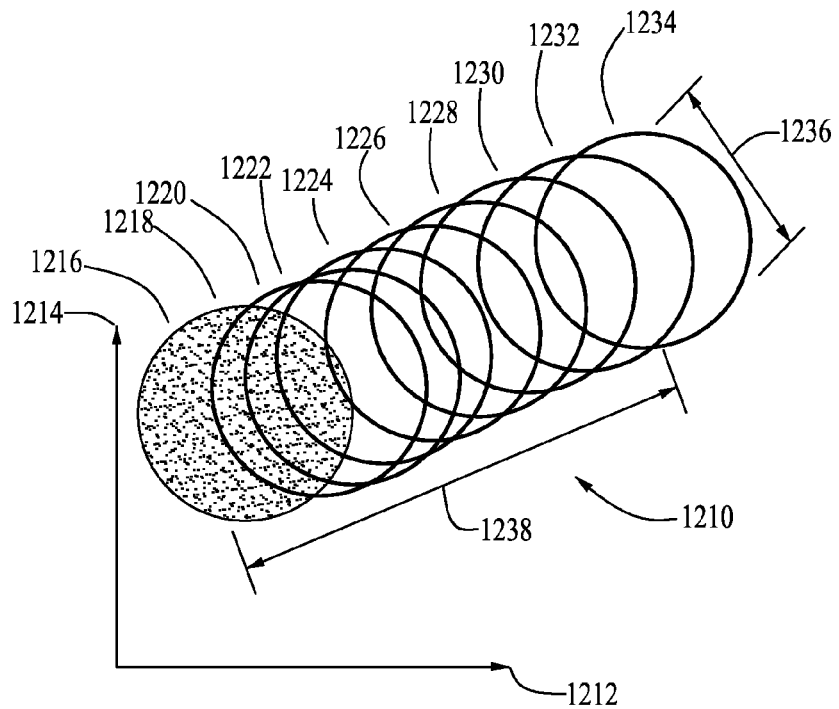
Figure 13:
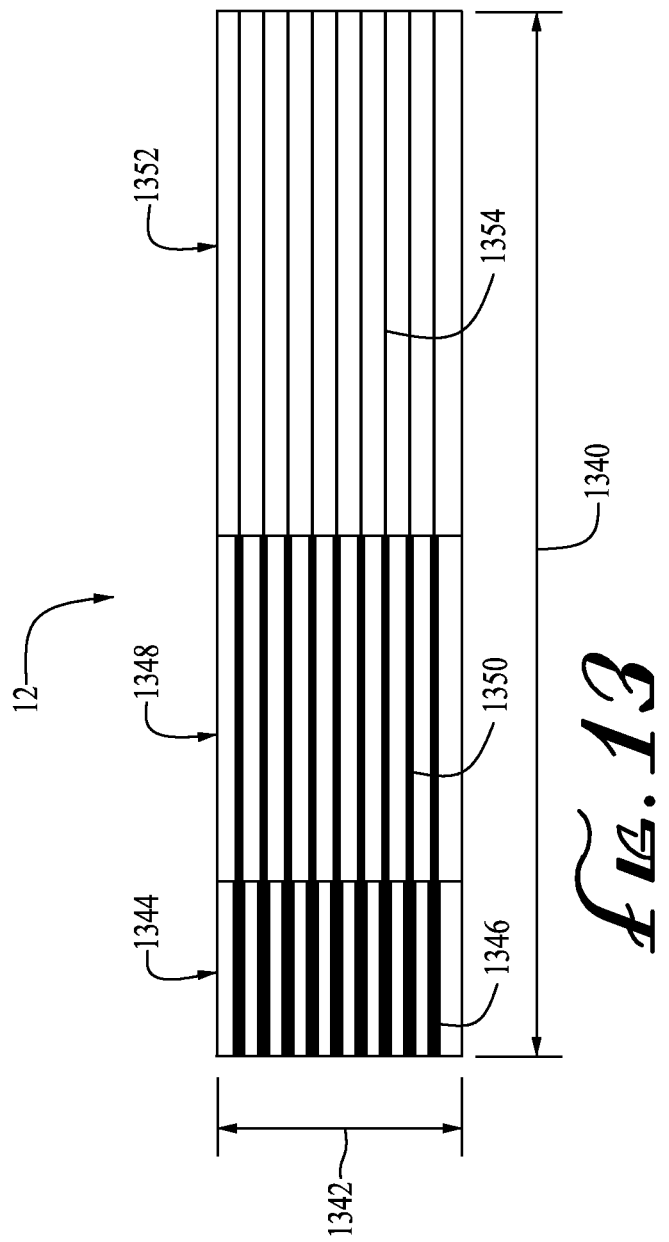
Figure 14:
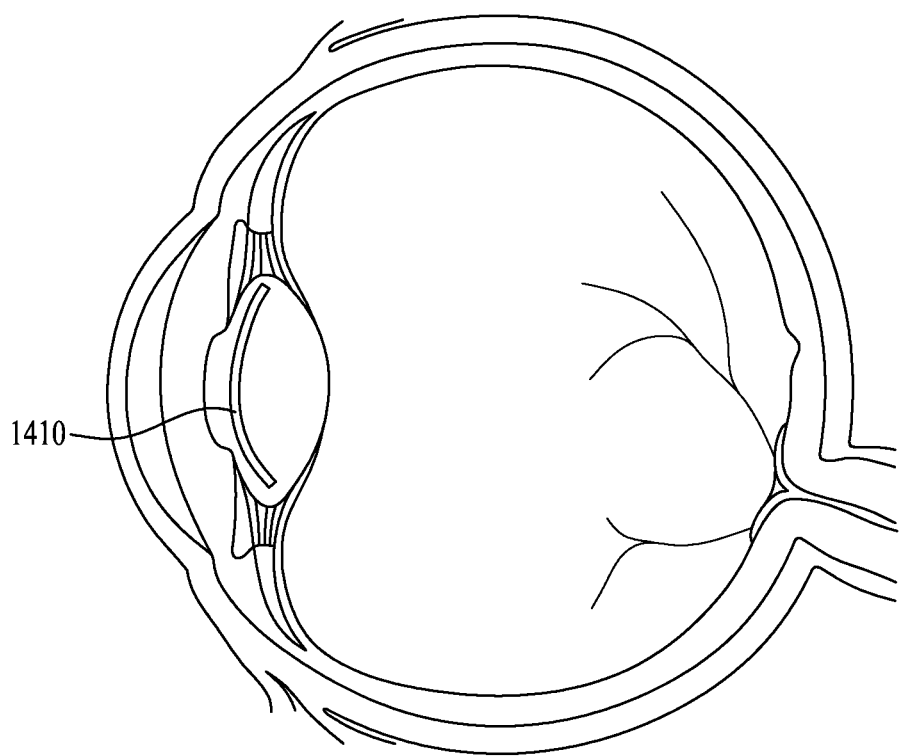

FIG. 2 schematically shows a portion of the body of an intraocular lens having two layers of modified loci;

FIG. 3 schematically shows a lens body having multiple layers of modified loci, where some of the layers are formed after placement of the lens in an eye;

FIG. 4A is a schematic view of one layer of the lens of FIG. 1 modified to generate a spherical focusing effect;

FIG. 4B is a top plan view of the layer shown in FIG. 4A;

FIG. 4C is a schematic view of a layer of the lens of FIG. 1 modified to generate an aspherical focusing effect;

FIG. 4D is a schematic view of a layer of the lens of FIG. 1 providing a defocusing meridian to accommodate for astigmatism;

FIG. 4E is a schematic top plan view of the layer of the lens of FIG. 4D at the horizontal meridian;

FIGS. 5 and 6 schematically show the principles utilized for forming the modified loci;

FIG. 7 schematically shows the layout of an apparatus according to the present invention for forming the aforementioned lenses;

FIG. 8 shows a flow chart for an algorithm useful in the apparatus of FIG. 7;

FIG. 9 graphically shows the effect of including a UV absorber in material used for forming a lens;

FIG. 10A graphically shows the relationship between the change of the index of refraction of modified loci as a function of laser pulse energy;

FIG. 10B graphically shows the relationship between the change in refractive index of a modified lens as a function of the number of laser beam pulses at a fixed pulse energy;

FIG. 11 schematically represents forming a lens according to the present invention using a layered raster-scan method;

FIG. 12 schematically represents forming a lens according to the present invention using a layered flying spot scanning method;

FIG. 13 schematically shows a process for creating a refractive layer structure by point wise variation of a change in refractive index; and FIG. 14 schematically shows how a natural lens can be modified in situ.

DESCRIPTION

Overview

In accordance with the present invention, a customized intraocular lens, referred to as a Customized Intraocular Phase Shifting Membrane (C-IPSM), is manufactured using a laser unit that generates a pulsed laser beam. More specifically, a laser unit optionally can generate laser beam pulses at 50 MHz, with each pulse having duration of about 100 femtoseconds and an energy level of about 0.2 to about one nanojoule. As envisioned for the present invention, the focal spot of the laser beam is moved over a surface of plastic material having a refractive index "$n_o$". This alters a sub-surface layer by creating a pattern of changes in the refractive index of the material ($\Delta n$).

Preferably, the customized intraocular lens (C-IPSM) is fabricated from a flat sheet of plastic that has a first side and a second side, and a thickness of from about 50 to about 400 mm between the two sides. During the manufacture of the customized intraocular lens (C-IPSM), the laser unit alters a sub-surface layer having a depth of only about 50 microns. The purpose of the layer of altered material in the layer is to compensate for optical aberrations of the patient to receive the C-IPSM. Specifically, this compensates for optical aberrations introduced into a light beam by an optical system (e.g., an eye).

The pattern of refractive index changes created in the plastic sheet results from exposing the plastic material to the electronic disruption and heat created by the layer in a predetermined manner. In particular, this change in refractive index is accomplished by sequentially focusing a laser beam onto a plethora of contiguous loci in the material. The result at each locus is an Optical Path Difference (OPD) for light passing through the spot. For a given material (e.g., plastic), having a given change in refractive index ($\Delta n$) (e.g., $\Delta n = 0.01$), and for a given distance through the material (e.g., 5 microns), an OPD (i.e., phase change) for light of a wavelength ($\lambda$) can be established. In particular, an OPD of $\lambda/10$ can be established for each 5 microns of locus depth. Thus, depending on the required refraction for each spot, the spot depth will be between 5 and 50 microns.

The amount of change in refractive index ($\Delta n$) can be altered for different locus positions, e.g., between a lowest value of $\Delta n = 0.001$ to a highest value of $\Delta n = 0.01$. Thus, depending on the required refraction, a value between $\Delta n = 0.001$ and $\Delta n = 0.01$ can be used, exploiting a modulo $2\pi$ phase wrapping technique.

Each locus can be created with the laser unit using a predetermined number of laser bursts (i.e., an "i" number of bursts). Preferably, each burst includes approximately 50 pulses and is approximately 1 microsecond in duration. During each burst, an alteration of a substantially cylindrical volume of material occurs through a depth of approximately five microns with a diameter of about one micron. Thus a locus contains at least one site, and typically up to 10 sites. In general, each burst causes an OPD of about one-tenth of a wavelength ($\lambda/10$). For "i" bursts: OPD=i(x($\lambda/10$)). Preferably, for the present invention there is approximately a $\lambda/10$ change for every 5 microns of locus depth (i.e., "i" is in a range of 1 to 10). For example, consider a situation wherein it is desired to create an OPD of $0.3\lambda$. In this case the laser unit is focused for an initial burst at a depth of twenty microns (i.e., i=3). Thereafter, the laser unit is refocused onto the locus two more times, with the focal point of the laser beam being withdrawn each time through a distance of five microns for each subsequent burst. The number "i" is selected depending on the amount of refraction that is desired at the locus (e.g., $0.2\lambda$ for i=2; and $0.7\lambda$ for i=7). A locus can be created by advancing, rather than withdrawing, the focal point of the laser beam.

In accordance with another version of the invention, employing variations of $\Delta n$, each locus is created with the laser unit using a varying number of pulses per laser burst. Each laser burst creates a site, there being from 1 to 10 sites per locus. Preferably, each burst includes between 5 pulses and 50 pulses and is approximately 100 nanoseconds to 1 microsecond in duration. During each burst, an alteration of a substantially cylindrical volume of material occurs through a depth of approximately five microns with a diameter of about one micron. In general, as mentioned above, each burst causes an OPD of about one-hundreds of a wavelength ($\lambda/100$) to one-tenth of a wavelength ($\lambda/10$). Thus, by maintaining a certain number of pulses per burst per spot, for example 5 pulses, on each subsequent location for one particular spot, a predetermined OPD, in this example one-tenth of a wavelength ($\lambda/10$), resulting from (10×($\lambda/100$)), is obtained. Variations in OPD are incurred via the change in $\Delta n$ from locus to locus, as the femtosecond laser beam is moved in a transverse direction, i.e., parallel to the surface of the plastic membrane.

Once the refractive properties desired for the customized intraocular lens (C-IPSM) are determined, a template of the anterior surface layer of the intraocular lens is calculated. This information is then sent to a manufacturing station and used for programming the individual pixels of the layers of the intraocular lens. Subsequently, after implantation of this customized intraocular lens, incoming light is refracted by the optical components in the pseudophakic eye to form an improved image on the retina of the eye.

The refraction of an incoming beam by the customized intraocular lens (C-IPSM) makes the optical path lengths of individual beams in any incoming beam appear to be substantially equal to each other. In this way, an incoming beam which carries the image information, is compensated by the customized intraocular lens (C-IPSM) to account for the refractive aberrations of the pseudophakic eye that are evidenced by the appropriate measurement data.

With regard to the optical performance of the micro-structured surface layer of the customized intraocular lens (C-IPSM), several refractive and diffractive optical principles can be employed for different modifications of the performance of the customized intraocular lens (C—IPSM). The designs comprise refractive, with or without phase wrapping, and diffractive phase ("GRIN") structures. Spherical, aspherical, achromatic, bifocal and multifocal embodiments are possible.

Lenses

Lenses having features of the present invention can be of any type of lens implanted in the eye, including contact lenses, intraocular lenses placed in the anterior or posterior chamber, and corneal lenses. IOLs placed in the posterior chamber often can be phakic when the natural crystalline lens is present and pseudophakic where the natural crystalline lens has been removed such as by cataract surgery. The invention is also useful for modifying lenses in situ, including lenses such as contact lenses in the anterior chamber, IOLs in the posterior chamber or anterior chamber, the natural cornea and natural crystalline lenses.

Figure 1B:
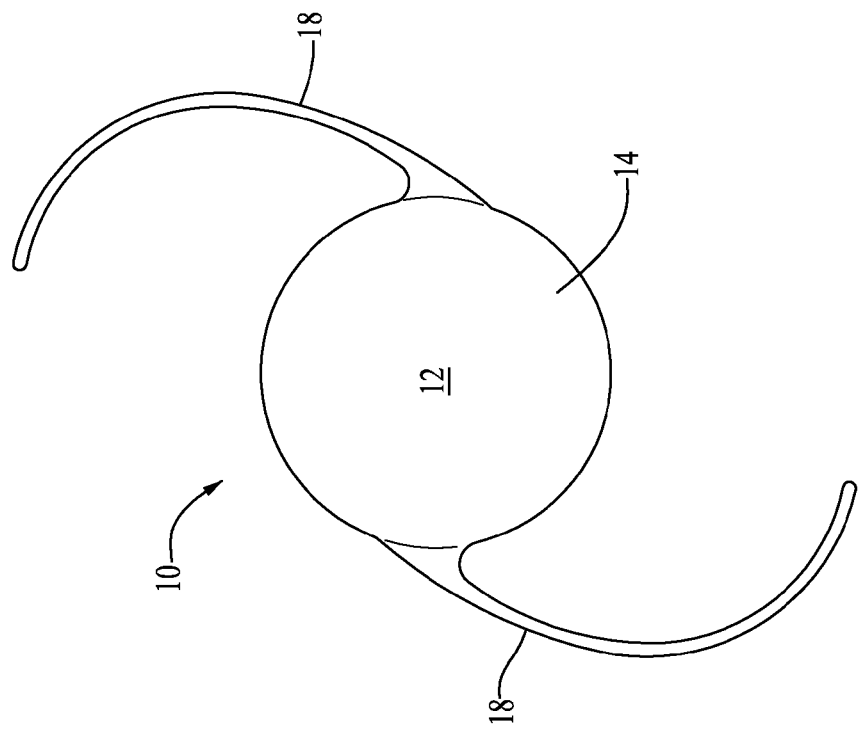
FIG. 1B is a top plan view of the lens of FIG. 1A.
Figure 1A:
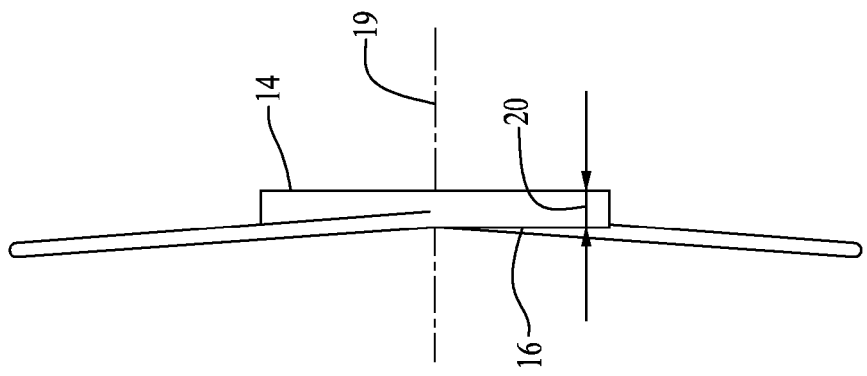
FIG. 1A is a front elevation view of an intraocular lens having features of the present invention.

With regard to FIGS. 1A and 1B, an intraocular lens 10 having features of the present invention comprises a central disc shaped body 12 having an anterior surface 14 and a posterior surface 16. Preferably both the anterior surface 14 and posterior surface 16 are substantially planar, i.e., they have little or no curvature such as concave or convex curvature. Use of the techniques of the present invention allows a plano-plano intraocular lens to be formed. As is conventional with many intraocular lenses, there can be a pair of haptics 18 for holding the lens in the posterior chamber The terms "anterior" and "posterior" refer to surfaces of a lens as it is normally placed in the human eye, with the anterior surface 14 facing outwardly, and the posterior surface 16 facing inwardly toward the retina. The lens 10 has an optical axis 19, which is an imaginary line that defines the path along which light propagates through the lens 10. In a version of the invention shown in FIGS. 1A and 1B, the optical axis 19 is coincident with the lens's mechanical axis, but this is not required.

Although it is preferred that all of the optical effects of the lens be provided by modified locus in the body 12, as described below, it is possible that corrective optical effects can also be provided in the conventional way, such as by having the anterior surface, the posterior surface, or both curved, such as convex, concave, or complex curvature. It is not necessary that all optical corrections be provided by modified loci according to the present invention, although that is the preferred.

A lens having features of the present invention can be used for correcting vision errors, such as for myopia (near-sighted), hyperopia (far-sighted), and astigmatism. The lens can be aspheric and/or toric.

The body 12 of the lens 10 is made of an optical material, which is any material presently existing or existing in the future that is suitable for making a lens for implantation in an eye. Typically the material is polymeric. The material used for the body 12 shows a change of refractive index when treated with a laser, as described in detail below.

Non-limiting examples of such materials include those used in the manufacture of ophthalmic devices, such as contact lenses and IOLs. For example, the present invention can be applied to siloxy-containing polymers, acrylic polymers, other hydrophilic or hydrophobic polymers, copolymers thereof, and mixtures thereof.

Non-limiting example of siloxy-containing polymers that can be used as optical materials are described in U.S. Pat. Nos. 6,762,271; 6,770,728; 6,777,522; 6,849,671; 6,858,218; 6,881,809; 6,908,978; 6,951,914; 7,005,494; 7,022,749; 7,033,391; and 7,037,954.

Non-limiting examples of hydrophilic polymers include polymers comprising units of N-vinylpyrrolidone, 2-hydroxyethyl methacrylate, N,N-dimethylacrylamide, methacrylic acid, poly(ethylene glycol monomethacrylate), 1,4-butanediol monovinyl ether, 2-aminoethyl vinyl ether, di(ethylene glycol)monovinyl ether, ethylene glycol butyl vinyl ether, ethylene glycol monovinyl ether, glycidyl vinyl ether, glyceryl vinyl ether, vinyl carbonate, and vinyl carbamate.

Non-limiting examples of hydrophobic polymers include polymers comprising units of $C_1$-$C_{10}$ alkyl methacrylates (e.g., methyl methacrylate, ethyl methacrylate, propyl methacrylate, butyl methacrylate, octyl methacrylate, or 2-ethylhexyl methacrylate; preferably, methyl methacrylate to control mechanical properties), $C_1$-$C_{10}$ alkyl acrylates (e.g., methyl acrylate, ethyl acrylate, propyl acrylate, or hexyl acrylate; preferably, butyl acrylate to control mechanical properties), $C_6$-$C_{40}$ arylalkyl acrylates (e.g., 2-phenylethyl acrylate, benzyl acrylate, 3-phenylpropyl acrylate, 4-phenylbutyl acrylate, 5-phenylpentyl acrylate, 8-phenyloctyl acrylate, or 2-phenylethoxy acrylae; preferably, 2-phenylethyl acrylate to increase refractive index), and $C_6$-$C_{40}$ arylalkyl methacrylates (e.g., 2-phenylethyl methacrylate, 3-phenylpropyl methacrylate, 4-phenylbutyl methacrylate, 5-phenylpentyl methacrylate, 8-phenyloctyl methacrylate, 2-phenoxyethyl methacrylate, 3,3-diphenylpropyl methacrylate, 2-(1-naphthylethyl)methactylate, benzyl methacrylate, or 2-(2-naphthylethyl)methacrylate; preferably, 2-phenylethyl methacrylate to increase refractive index).

A preferred material is a hydrophobic acrylic polymer made from N-benzyl-N-isopropylacrylamide, ethyl methacrylate, and butyl acrylate cross linked by ethylene glycol dimethacrylate.

The material can optionally contain a ultraviolet light blocker, such as acrylic derivatives of benzotriozoles.

For a typical IOL, the body 12 has a diameter of about 6 mm and preferably has a thickness 20 of from about 50 μm to about 400 μm, and most preferably about 250 μm. This is a smaller thickness than with conventional IOLs. When the lens 10 is folded to be placed in the posterior chamber, because of its relative thinness, it is possible for a surgeon to make a smaller incision than with conventional lenses. This can increase safety for the patient, and it is believed can result in reduced post-operative recovery time, and reduced surgically induced astigmatism. Also in the version of the invention where the anterior and posterior surfaces are planar, it is easy to insert the lens, thereby rendering some instances of cataract surgery less traumatic.

The optical effect provided by the lens 10 is a result of the presence of modified loci in the body 12, where the modified loci having been formed by a laser beam that causes the modified loci to have a different refractive index than the lens material before modification.

FIG. 2 shows a portion of an exemplary lens body 12 having two spaced apart planar layers generally parallel to the anterior surface 14 of the lens body 12, an upper layer 22 and a lower layer 23. Layers 22 and 23 are preferably 50 μm in thickness. Only a portion of each layer is shown, and exemplary modified loci are shown only for the upper layer 22. Layer 22 contains exemplary contiguous modified loci 24a-24j. Each locus 24 is cylindrical shape with a diameter of about 1 μm with its axis generally parallel to the optical axis 19 of the lens. Each locus 24a-j contains one or more sites 26 formed by a single pulse from a laser. Each site is typically about 5 μm in height, and thus the modified loci range in height from about 5 to about 50 μm. As shown in FIG. 2, locus 24a contains 10 sites 26, locus 24b contains 9 sites, continuing to locus 24j which contains one site.

The change in refractive index of the material present in the modified loci results in a change in the optical path length. In particular, the optical path length of each modified locus is increased by about 0.1 wave as compared to the optical path length of a non-modified locus, with respect to light of a selected wavelength. Generally green light having a wavelength of about 555 nm is the basis for modification since the light of that wavelength is typically optimally received by the human eye. Thus each modified locus has an optical path length of about 0.1 to about 1 wave greater than the optical path length of a non-modified locus, wherein the wavelength is with respect to light of wavelength of 555 nm.

Preferably there are sufficient modified loci that at least 90%, and more preferably at least 99%, of the light projected onto the anterior surface 14 of the lens 10 in a direction generally parallel to the optical axis 19 passes through at least one modified locus 24.

FIG. 3 shows a schematic view of the multilayered, microstructured customized intraocular lens 10 that is membrane-shaped, exhibiting a disc-like planar appearance, with a diameter 62 of about 6 mm and a width 64 of about 500 μm. The refractive properties of the micro-structured customized intraocular lens are inscribed in thin layers, indicated as 66 to 88, which are typically 50 μm thick. Initially, a posterior layer, e.g., between the posterior surface 16 and plane 69, at depth 65, is generated. The layers 72, 74, 76, 78, 80, 82, 84, 86 and 88 are micro-structured accordingly. Additional layers 66, 68 and 70 can be micro-structured during an in-vivo fine-tuning procedure of the refractive properties of the implanted customized intraocular lens, covering the anterior portion of the intraocular phase-shifting membrane between planes 69 and 71, having a thickness 67.

Each layer 66-88 contains modified loci, and typically more than 1,000,000 modified loci, and up to about 30,000,000 loci, and each layer typically is in a plane substantially parallel to the anterior surface 14 of the lens body 14.

FIG. 4 shows pattern of modified loci used for achieving different optical effects. The layer shown in FIGS. 4A and 4B provide a spherical adjustment in the amount of about +0.4 diopter. It comprises three annular rings, 402, 404, and 406 concentric with the optical axis 19 and surrounding a central region 408. Thus the modified loci are in a circular pattern concentric with the optical axis. The outer edge of the outermost radius ring 402 is at $r_4$, which is 3 mm from the optical axis 19, i.e., it is at the peripheral edge of the body 12. The outside edge of the second ring 404, $r_3$, is 2.5 mm from the optical axis 19. The outside edge of the third ring 406, is at $r_2$ which is 2 mm from the optical axis 19. The central portion 408 outside edge $r_1$ is at 1.4 mm. Each ring is made of plurality of contiguous modified loci wherein the number of sites in each locus increases as the locus is closer is to the optical axis 19. Thus the modified loci at the outer edge of the first ring 402 has one site, and thus a height of about 5 μm, while the modified locus closest to the optical axis 19 has 10 sites, and thus is about 50 μm in height.

The layer shown in FIG. 4C is patterned to provide an aspherical focusing effect. In this layer, the inner most ring 406' and the central region 408' have the same pattern as the ring 406 and the central region 408, respectively, in FIG. 4A. However, the outer rings 402' and 404' have the modified loci reversed in that there are more sites in the modified loci farther from the optical axis 19 than there are for modified loci radially inwardly. Because $r_1$, $r_2$, and $r_3$ are the same in the version shown in FIG. 4C as in 4A, the top plan schematic view of 4B is also applicable to the layout shown in FIG. 4C.

FIG. 4D shows a pattern for the modified loci to accommodate for astigmatism and/or toricity taken at the horizontal meridian of the lens. In this version, all the rings 402", 404", and 406", and the central region 408" decrease in height the closer the modified loci in any single ring is closer to the optical axis 19, exhibiting a defocusing effect in the horizontal meridian.

The top planar view of the layer of FIG. 4D is shown in FIG. 4E wherein the layer shown in FIG. 4D is positioned horizontally. The vertical meridian of the astigmatic connecting layer of FIG. 4D is the same as shown in FIG. 4A. The horizontal meridian provides −0.4 diopter power and the vertical meridian provides +0.4 diopter power. At the 45° diagonals, there is no refraction effect.

There are smooth transitions between the various regions of the layer depicted.

Each locus has a very small diameter, on the order of about 1 μm. The transition from the outside of a ring to the inside of a ring need not be a steady step wise decrease in the number of sites because there can be multiple modified loci having the same number of sites adjacent to each other.

The optical effect provided by the lens 10 can be easily increased or decreased by changing the number of rings. For example, with the lens schematically shown in FIG. 4A, each ring provides a 0.1 dioptic power, and thus the lens shown in FIG. 4A provides 0.4 dioptic power. To make a lens having a 10 dioptic power, where each ring contributes 0.1 diopter, the lens is made with about 100 rings, where 99 of the rings have the same general configuration of rings 402, 404, and 406 in FIG. 4A, and the center ring has the configuration of the center ring 408 shown in FIG. 4A. However, since there are more rings in the same surface area, each ring has a much smaller width than the rings in FIG. 4A.

FIGS. 5 and 6 demonstrate the principle of a modulo-$2\pi$ phase wrapping technique that can be used to characterize the present invention. Specifically, the formed microstructure is generated to compensate for optical path length differences within an array of neighboring rays, e.g., rays 542, 544 and 546, such that all of the contiguous individual light beams 542, 544 and 546 are in phase with each other. For the discussion here, the individual contiguous light beams 542, 544 and 546 are considered exemplary.

In FIG. 5, the sinusoidal characteristic of a first light beam 542 and second light beam 544 are shown as a function of time. If the light beams 542 and 544 were in phase with each other, which they are not in FIG. 5, the second light beam 544 would be shown superimposed on top of the first light beam 542. As shown, however, the light beams 542 and 544 are out-of-phase relative to each other, and this difference in phase is shown as a phase shift 590. Conceptually, the phase shift 590 can be thought of as either a difference in time or a difference in distance traveled. For instance, at the specific point in time 592, the first light beam 542 is at a certain position in free space. Due to the phase shift 590, however, the second light beam 544 is not at this same position until the subsequent point in time 594. For the situation shown in FIG. 5, and when considering that the first light beam 542 will go through a complete period, or cycle, of 360° ($2\pi$ radians) as it travels from the point in time 592 to a point in time 596, that the magnitude of the phase shift 590 between the first light beam 542 and the second light beam 544 is less than $2\pi$.

With regard to the first light beam 542 and a third light beam 546 depicted in FIG. 6, the point in time 592 for first light beam 542 corresponds to the point in time 598 for the third light beam 546. Thus, the total phase shift 604 which exists between the first light beam 542 and the third light beam 546 is more than $2\pi$. As contemplated, for the present invention, the total phase shift 604 actually includes a modular phase shift 500 which is equal to $2\pi$, and an individual phase shift 502 which is less than $2\pi$. Using this notation, the total phase shift 604 between any two light beams can be expressed as the sum of a modular phase shift 500 which is equal to n$2\pi$, where "n" is an integer, and an individual phase shift 502, the so-called modulo $2\pi$ phase shift, which is less than $2\pi$. Thus, the integer "n" may take on different values (e.g., 0, 1, 2, 3, . . . ) and, specifically, for the light beam 544 (FIG. 3A) n=0, while for the light beam 546 (FIG. 3B) n=1. In all cases, the total phase shift 604 for each light beam 544, 546, is determined by comparing it with the corresponding light beam 542 as a reference. The modular phase shift 500 can then be subtracted from the total phase shift 604 to obtain the individual phase shift 502 for the particular light beam 544, 546. First, however, the total phase shift 604 is determined.

Referring to FIG. 4A, at each locus the modular phase shift 500 ($=n \times 2\pi$) is subtracted from the total phase shift 604, to yield the individual phase shift 502, e.g., in FIG. 4A, the modular phase shift 500 amounts to $0 \times 2\pi = 0$ in the center zone, $1 \times 2\pi$ in the second zone ($r_1$ to $r_2$), $2 \times 2\pi = 4\pi$ in the third zone ($r_2$ to $r_3$) and $3 \times 2\pi = 6\pi$ in the fourth zone ($r_3$ to $r_4$). The individual phase shifts 502 (0 to $2\pi$, corresponding to 0.0 to 1.0 waves), are inscribed into the loci, amounting to 5 µm to 50 µm depth.

Thus, with further reference to FIG. 4A the local phase-shift in dependence of the distance from the pupillary axis is plotted, as imposed by the micro-structured customized intraocular lens, changing from a phase-shift of $2\pi$, equivalent to 1.0 waves, at the optical axis 19 is to zero at the radial position $r_1$. It is assumed, that the initial optical beam, impinging on a micro-structured customized intraocular lens is collimated, exhibiting individual rays with identical optical path lengths, shaping a planar optical wave. As a result of the travel of the individual rays through the micro-structured customized intraocular lens, a focused optical wave is generated. In the center part of the optical beam, inside an area limited by the radius $r_1$, the optical phase shift changes quadratically with respect to the distance from the optical axis. At position $r_1$, a phase-shift of zero, equivalent to 0.0 waves, is implemented. The adjacent ray, laterally from radius $r_1$, is subjected to a phase-shift of $2\pi$, equivalent to 1.0 waves, resulting in the characteristic phase-jumps of $2\pi$, equivalent to 1.0 waves, at the zone boundaries of a modulo $2\pi$ phase wrapping technique. With regard to FIG. 5, such phase jumps by an amount of $2\pi$, respectively a multiple of $2\pi$ ("shift 500") can be visualized as "catching the next wave" which is delayed by one full cycle 2n, as related to the adjacent light beam. In general, at each of the radial positions $r_1$, $r_3$, $r_4$, the local phase-shift jumps by $2\pi$, corresponding to 1.0 waves, whereas in between these jumps the phase changes quadratically, from a value of $2\pi$ equivalent to 1.0 waves, to zero, equivalent of 0.0 waves.

Generally there are sufficient modified loci that the refractive index of the body has been modified sufficiently to change the dioptic power of the body by at least +0.5 (+0.5 to +X) or at least −0.5 (−0.5 to −Y) where X can be about 48 and Y can be about 15.

In the multilayer versions of the invention, typically the layers are spaced-apart by at least one micron, and preferably by at least 5 µm.

In the multilayer version, it is possible to optimize the various layers for a particular selected wavelength of light. For example, a first layer can be optimized for the light of a first wavelength, such as green, the second layer for light of a second wavelength, which differs from the first wavelength by at least 50 nm, such as red light, and a third layer can be optimized for light of a third wavelength that differs from both the first and second by at least 50 nm, such as blue light.

Also different layers can be formed to focus light at different focal spots.

Another use of multi layers is to have a single layer perform multiple optical corrections rather than have all vision corrections in a single layer. Thus it is possible to have a first layer provide a diopter adjustment, and other layers provide other optical corrections such as a toric adjustment or an aspheric adjustment. Thus the first layer can provide a diopter adjustment, the second layer loci can provide a toric adjustment, and a third layer can provide an aspheric adjustment.

System for Making and Modifying Lenses

The present invention uses very short laser pulses of sufficient energy tightly focused on an optical, polymeric material to form the lenses. High intensity of light at the focus point causes a nonlinear absorption of photons (typically multi-photon absorption) and leads to a change in the refractive index of the material at the focus point. The region of the material just outside the focal region is minimally affected by the laser light. Accordingly, select regions of an optical, polymeric material are modified with a laser resulting in a positive change in the refractive index in these regions.

Thus lenses can be formed by irradiating select regions of an optical, polymeric material with a focused, visible or near-IR laser having a pulse energy from 0.05 nJ to 1000 nJ. The irradiated regions exhibit little or no scattering loss, which means that the structures formed in the irradiated regions are not clearly visible under appropriate magnification without contrast enhancement.

The pulse energy of the focused laser used in the method in-part depends on the type of optical material that is being irradiated, how much of a change in refractive index is desired and the type of structures one wants to imprint within the material. The selected pulse energy also depends upon the scan rate at which the structures are written into the optical material. Typically, greater pulse energies are needed for greater scan rates. For example, some materials call for a pulse energy from 0.2 nJ to 100 nJ, whereas other optical materials call for a pulse energy from 0.5 nJ to 10 nJ.

The pulse width is preserved so that the pulse peak power is strong enough to exceed the nonlinear absorption threshold of the optical material. However, the glass of a focusing objective used can significantly increase the pulse width due to the positive dispersion of the glass. A compensation scheme is used to provide a corresponding negative dispersion that can compensate for the positive dispersion introduced by the focusing objective(s). Accordingly, the term "focused" in this application refers to the focusing of light from a laser within an optical, polymeric material using a compensation scheme to correct for the positive dispersion introduced by the focusing objective(s). The compensation scheme can include an optical arrangement selected from the group consisting of at least two prisms and at least one mirror, at least two diffraction gratings, a chirped mirror and dispersion compensating mirrors to compensate for the positive dispersion introduced by the focus objective The use of the compensation scheme with the focusing objective can generate pulses with pulse energy from 0.01 nJ to 100 nJ, or from 0.01 nJ to 50 nJ, and a pulse width of from 4 fs to 200 fs. At times, it can be advantageous to generate a laser pulse with energies from 0.2 nJ to 20 nJ, and a pulse width of from 4 fs to 100 fs. Alternatively, it can be advantageous to generate a laser pulse with energies from 0.2 nJ to 10 nJ and a pulse width of from 5 fs to 50 fs.

The laser can generate light with a wavelength in the range from violet to near-infrared radiation. In various embodiments, the wavelength of the laser is in the range from 400 nm to 1500 nm, from 400 nm to 1200 nm or from 600 nm to 900 nm.

FIG. 7 schematically shows a preferred apparatus 702 for forming modified loci. The apparatus 702 comprises a laser 704, preferably a femtosecond laser as used in 2-photon microscopes, a control unit 706, a scanning unit 708, a holder 710 for the lens disc 12, and means 712 for moving the disc 12 in which modified loci are being formed. A suitable laser is available from Calmar Laser, Inc, Sunnyvale, Calif. Each pulse emitted by the laser can have a duration of from about 50 to about 100 femtoseconds and an energy level of at least about 0.2 nJ. Preferably the laser 704 generates about 50 million pulses per second at a wavelength of 780 nm, a pulse length of about 50 fs, each pulse having a pulse energy of about 10 nJ, the laser being a 500 mW laser. An emitted laser beam 721 is directed by a turning mirror 722 through an acustooptic modulator 724 that controls the frequency of the pulses, typically at about 50 MHz to 100 MHz repetition rate. The laser beam 721 typically has a diameter of 2 mm when emitted by the laser. The laser beam 721 then travels through the scanning unit 708 that spatially distributes the pulses into a manifold of beams. The pattern can be a raster-scan pattern or flying spot pattern. The scanning unit 708 is controlled by a computer control system 726 to provide the desired configuration of the modified loci in the disc 12.

The beam 721 emitted from the laser has a diameter from about 2 to about 2.5 nm. The beam 721, after exiting the scanner 708, is then focused to a size suitable for forming modified loci, typically forming loci having a diameter from about 1 to about 3 μm. The focusing can be effected with a telescopic lens pair 742 and 744, and a microscopic objective 746, where another turning mirror 748 directs the beam from the lens pair to the microscopic objective. The focusing microscope objective can be a 40×/0.8 objective with a working distance of 3.3 mm. The scanning and control unit are preferably a Heidelberg Spectralis HRA scanning unit available from Heidelberg Engineering located in Heidelberg, Germany.

The optics in the scanning unit allow a region having a diameter of about 150 to about 450 μm to be modified without having to move either the disc 14 or the optics. Typically, a single layer of 50 μm thickness can be micro-structured in a region in about one minute.

To modify other regions of the disc 12 it is necessary to move the holder 710 with the moving means 712. The moving means 712 allows movement in the "z" direction for providing modified loci in different layers, and also in the "x" and "y" directions for treating different regions at the same depth. The moving means 712 serves as a precise positioning system to cover the full diameter of an intraocular disk, which typically has a diameter of 6 mm.

The holder 710 can be a bracket, a conveyor belt with recesses sized for the lens, a tray having recesses for the lens, and any other structure that can hold the lens sufficiently stable for formation of a desired refraction pattern.

The moving means can be any mechanical structure, typically driven by motors, that provide movement in the x, y and z directions, i.e., three dimensional movement. The motors can be stepper motors. Typically movement is up to about 10 mm/second.

The lens manufacturing procedure uses stepping via xyz-positioning from one scan-field (typically 450 μm diameter) to the next scan-field of the 2-photon microscope (raster-scan or flying spot scan). The 2-photon microscope provides the depth-scan. Typically, one refractive layer can be completed within the range of the 2-photon microscope. Alternatively, the z-positioning is provided by mechanical z-positioning, in order to provide extended reach to deeper layers in disc 14.

The control unit 706 can be any computer that includes storage memory, a processor, a display, and input means such as a mouse, and/or keyboard. The control unit is programmed to provide the desired pattern of the modified loci in the disc 12 by providing control instructions to the scanning unit 708, and when necessary to the moving means 712.

An exemplary program for forming a disc is shown in FIG. 8, where the beam is maintained stationary (i.e., the scanner is not used) and the target disc is moved mechanically. When the program commences, the user is prompted to select the desired lens in step 801. Next, the user provides the desired speed for scanning the disc 14 during the laser pulsing in step 802. Only when the computer determines this speed is a safe speed, typically 4 mm or less of travel per second, does the program accept the input in step 803. The program next sets the laser to use maximal power, and prompts the user for confirmation to continue in step 804. At this stage the program provides the user a last opportunity to avoid lens writing before in step 805. If the user has chosen to abort writing, the program terminates. Otherwise, the program modifies a log file in step 806 to record variables appropriate to record keeping and advances.

The laser begins in a position at one extreme in both the x and y directions, which constitutes the home position. Each layer in a modified lens can be thought of as a stack of minilayers of a depth equal to the thickness of a site. On a given minilayer, the laser advances across one dimension (e.g., x), while holding the other two (e.g., y and z) constant, thereby writing a series of sites. The program begins each series by finding a grid location that constitutes the starting point of the current series in step 807. Next, the program writes that series wherever appropriate in step 808. When the program has scanned the laser to the outer extent of a given series, it amends the log file to reflect that the series is complete in step 809. The program then queries the input instructions to determine if there are subsequent series to be formed in step 810. This process continues until all series of modified loci in a given minilayer are formed. Whenever a new series needs to be prepared, the program advances the second variable (e.g. y), and resets the first dimension (e.g. x) to begin a new series 807. Once the laser has finished scanning across all grid locations of the minilayer, having considered each successively and having written the series when appropriate, the program is done with writing for that minilayer. The scanner then resets the first and second dimensions to their original positions in step 811, thereby returning the laser to its home position. The program updates the log file to show that the layer is complete in step 812.

The program then queries to determine if more minilayers are necessary in step 813 to achieve the user's desired lens. If more minilayers are needed, the program advances the third dimension (e.g., z) and repeats the above process, beginning with finding the first grid location for the first line of the new layer 817. If no more minilayers are necessary, the program returns the laser to its original, home position for all three dimensions in step 814, modifies the log file to reflect both that writing is complete and the system time in step 815, and terminates execution. Once a layer, which typically has from 1 to 10 minilayers is completed, then any additional layer that needs preparation can be prepared using the same process. In an optional program, the focus point of the scanner 708 can be moved in the z direction (depth) to form deeper sites. Generally all sites at the same depth are formed, and then all sites at the next depth within a layer are formed, until all the sites in a layer are completed.

The storage memory can be one or more devices for storing data, including read-only memory (ROM), random access memory (RAM), magnetic disk storage mediums, optical storage mediums, flash memory devices, and/or other machine-readable mediums for storing information.

The control can be implemented by hardware, software, firmware, middleware, microcode, or a combination thereof. When implemented in software, firmware, middleware or microcode, the program code or code segments to perform the necessary tasks can be stored in a machine-readable medium such as a storage medium or other storage(s). A processor may perform the necessary tasks. A code segment may represent a procedure, a function, a subprogram, a program, a routine, a subroutine, a module, a software package, a class, or a combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted through a suitable means including memory sharing, message passing, token passing, network transmission, etc.

Optionally an adaptive-optics module (AO-module) can be used to simulate the effect of a refractive correction, with regard to image clarity and depth of focus. The AO-module can be composed of a phase-point compensator and an active mirror for the purpose of pre-compensating individual light beams generated by the laser 704. An adapted optics device to compensate for asymmetric aberrations in a beam of light is useful for the invention described in my U.S. Pat. No. 7,611, 244. A method and apparatus for pre-compensating the refractive properties of the human with an adaptive optical feedback control is described in my U.S. Pat. No. 6,155,684. Use of active mirrors is described in my U.S. Pat. No. 6,220, 707.

The optical resolution ($\Delta xy$, $\Delta z$) for a two-photon signal amounts to: $2\Delta xy = 2 \times (0.325\lambda)/(NA 0.91) = 622$ nm ($1/e^2$ diameter), $\Delta z = 2 \times 0.532\lambda \times 1/(n-\sqrt{n^2-NA^2}) = 3102$ nm (NA=Numerical Aperture, e.g., 0.8). This yields a site size.

Typical scan-fields in the raster scan mode amount to: 150 µm field of view: 1536×1536 pixels at 5 Hz or 786×786 pixels at 10 Hz; 300 µm field of view: 1536×1536 pixels at 5 Hz or 786.times.786 pixels at 9 Hz; 450 µm field of view: 1536× 1536 pixels at 5 Hz or 786×786 pixels at 9 Hz.

For quality control while forming the modified loci, the laser can be used to generate light from autofluorescence of the material of the lens. Modified loci generate more fluorescence than non-modified material. If a suitable increase in emitted fluorescence light is not detected, that indicates that the process for forming the modified loci is not proceeding properly. A suitable system for detecting autofluorescence is shown in FIG. 7 of my copending U.S. patent application Ser. No. 12/717,866 filed even date herewith, entitled "System for Characterizing A Cornea And Obtaining An Ophthalmic Lens". Also, the autofluorescence detected can be used for positioning the focal point of the system of the laser beam from the microscope objective 746 for forming additional loci, using detected modified loci has a reference position.

The optical effects provided by the lens 10 for any particular patient can be determined using conventional techniques for designing a lens. See for example the techniques described in U.S. Pat. No. 5,050,981 (Roffman); U.S. Pat. No. 5,589,982 (Faklis); U.S. Pat. No. 6,626,535 (Altman); U.S. Pat. No. 6,413,276 (Werblin); U.S. Pat. No. 6,511,180 (Guirao et al); and U.S. Pat. No. 7,241,311 (Norrby et al). A suitable technique is also described in my aforementioned copending U.S. patent application Ser. No. 12/717,866.

Optionally an absorber for light of the laser beam wavelength can be included in the disc to reduce the amount of energy required for forming the modified loci. It is desirable to have as little energy as possible used for this purpose, because exposure to excess energy can result in a cracking or other undesirable mechanical changes in the body 12. Exemplary of UV absorbers that can be used with the laser 704 are derivatives of benzotriozoles, such as 2-(5-chloro-2-H-benzotriazol-2-yl)-6-(1,1-dimethyl-ethyl)-4-(propyenyloxypropyl)phenol, and benzophenol derivatives, such as 3-vinyl-4-phenylazophenylamine, which is a yellow dye that absorbs at a wavelength of 390 nm. Preferably the amount of UV absorber provided is at least 0.01% by weight, and up to about 1% by weight of the material used for forming the lens body 12.

In FIG. 9, the threshold energy (I) (nJ) for achieving permanent structural change in plastic material in dependence of concentration (%) of an aromatic UV-absorber is shown. The typical characteristic demonstrates a strong dependence of the threshold energy on the concentration of the UV-absorber, indicating the enhancement of the local permanent structural change with the concentration of the UV-absorber, due to the increased probability of two-photon absorption processes at 390 nm wavelength, half the wavelength of the referenced incident femtosecond laser pulses of 780 nm. The local interaction of the molecules of the plastic host results in a localized, partial micro-crystallization of the plastic material, yielding an increase $\Delta n$ of the refractive index n. At a concentration of 0.8% of the UV-absorber, as used in commercial intraocular lens materials, a threshold energy of about 0.1 nJ is required. In contrast, in undoped, bulk plastic material, a threshold energy of about 1 nJ is necessary. The stated threshold energies are based on a spotsize of about 1 µm diameter, yielding threshold laser fluences of about 0.01 J/cm$^2$ and 0.1 J/cm$^2$, respectively.

FIG. 10 shows the laser-material interaction process for changing the refractive index of a plastic material with femtosecond laser pulses. In FIG. 10A, the change $\Delta n$ of the refractive index is plotted as function of the pulse energy; in FIG. 10B, the change $\Delta n$ of the refractive index is plotted as a function of the number of pulses in the focal area at a fixed pulse energy (e.g., 0.2 nJ). The curve 1050 in FIG. 10A demonstrates that with increasing pulse energy from 0.1 nJ to 8 nJ, the change $\Delta n$ of the refractive index n is enhanced from approximately 0.1% to approximately 1.0%. The threshold for the initial occurrence of a measurable change $\Delta n$ of the refractive index n is denoted at position 1052 of the curve 1050; at a pulse energy level of approximately 8 nJ, corresponding to a laser flux of approximately 0.8 J/cm.sup.2, the threshold for photo disruption of the plastic material is reached, resulting in collateral damage of the material and opacifications, facilitating undesirable scattering losses of the light that is transmitted through the plastic material. As can be seen from curve 1050, the range of possible pulse laser energies extends over two orders of magnitude, from 0.05 nJ to 8 nJ, allowing for a safe operation of the manufacturing process which occurs at the lower end of the range, at a pulse energy of approximately 0.2 nJ. In undoped plastic material, the safe range for a corresponding manufacturing process extends only over close to one order of magnitude. In addition, the low pulse energies, which are facilitated by the incorporation of the UV-absorber, allow for an especially smooth modification of the material properties, providing an intraocular phase-shifting membrane with extremely low light scattering losses. In FIG. 10B, the curve 1060 indicates that the cumulative effect of approximately 50 laser pulses in the focal volume yields refractive index changes $\Delta n$ of the order 1%, sufficient for achieving a optical path length difference (OPD=($\Delta n$)× thickness) of 1.0 waves in a plastic material layer of 50 µm thickness, choosing a low pulse energy of 0.2πJ.

In FIG. 11, the manufacturing process of an intraocular phase-shifting lens where the scanning unit 708 provides a raster-scan pattern is exemplified. A procedure exhibiting the successive positioning of ten adjacent minilayers, each field comprising a densely spaced raster scan pattern is demonstrated. A stack 1170 of raster-scan minilayers 1176, 1178, 1180, 1182, 1184, 1186, 1188, 1190, 1192, and 1194 is shown in an x-(1172) and y-(1174) coordinate system and extends over a thickness 1202 of approximately 50 µm, i.e., each minilayer amounts to approximately 5 μm. The lateral size of individual minilayers typically varies between 150 μm to 450 μm for x (1198) and y (1199) dimensions, allowing for a change in the overlay of laser pulses in the focal volume of 1 μm diameter per spot by a factor of ten. The surface 1996 is the end of a layer.

In FIG. 12, the manufacturing of an intraocular phase-shifting lens where the scanning unit 708 provides a layered flying spot pattern is presented. As an example, the successive positioning of ten tightly spaced circular scans is shown. A stack 1210 of circular scans 1216, 1218, 1220, 1222, 1224, 1226, 1228, 1230, 1232, and 1234 is shown in a x (1212) and y (1214) coordinate system and extends over a thickness 1238 of approximately 50 μm, i.e., the distance between individual circular scans or minilayers amounts to approximately 5 μm. The diameter 1236 of the circular scans can be from as small as a few microns to approximately 450 μm, so that the amount of overlay of laser pulses per resolvable spot can be changed over a wide range. The speed of the sequence of spots per line can be chosen as required, by changing the length of a scan line. Individual scan lines can exhibit various shapes. The resolution of the smallest scan details can comply with the resolution limit of the two-photon microscope of approximately 1 μm diameter, whereas the raster scan procedure, as described with regard to FIG. 11, is limited to a resolution of approximately 150 μm, as given by the smallest raster scan fields of a two-photon microscope. For practical applications, the manufacturing process of intraocular phase-shifting membrane is accomplished by the dual scan-system in a complimentary fashion: The bulk part of the process is performed with the time-optimal raster scan method, whereas the fine details of the required refractive properties are contributed by the flying spot scanner with its inherent high spatial resolution.

In FIG. 13, the creation of a refractive layered structure by pointwise variation of the refractive index change Δn is demonstrated. In general, the refractive structure is incorporated in a rectangularly shaped layer in the intraocular phase-shifting lens body 12. In FIG. 13, a portion of the intraocular phase-shifting membrane device is shown, comprised of e.g., three neighboring stripes 1344, 1348, 1350, and 1384 with a width of 150 μm, 300 μm and 450 μm, respectively. The overall dimensions of the region of body 14 amount to a width 1340 of 900 μm and a thickness 1342 of 50 μm. Since the standard number of pixels per scan line in x- and y-directions is chosen as 1536×1536 pixels, the densities of pulses per scan-line 1346, 1350, and 1354 amount to 10 pulses per micron, 5 pulses per micron and 3 pulses per micron, respectively, yielding a two-dimensional overlay factor of 100 pulses per spot, 25 pulses per spot and 9 pulses per spot, respectively.

In Situ Modification

Substantially the same method and apparatus discussed above can be used for modifying lenses in situ. This includes intraocular lenses, corneal lenses, corneal contact lenses, and natural crystalline lenses. In most instances, the lens already has optical features, such as dioptic power, toricity and/or asphericity. This method is useful for fine tuning lenses, and provides an option to LASIK surgery.

For an in situ modification, the apparatus of FIG. 7 is used, except there is no need for a lens holder 710 or means 712 for moving the lens. Rather, to the extent that the field of modification provided by the focusing system covers only a portion of the lens being modified, the focusing system can be changed to focus in additional regions. With reference to FIG. 14 a layer 1410 of about 6 mm in diameter of a natural lens can be modified using the apparatus of FIG. 7. The layer 1410 contains modified loci, each modified locus having from 1 to 10 sites. Typically a region of about 2 mm in diameter is modified as one scan field. Then the lens system of the apparatus of FIG. 7 is sequentially moved to modify additional regions. Each region can have one or more planes of modified loci.

The concept of customized lens design and in situ modification can be used to achieve customized refractive corrections in living human eyes by, for example, modifying the cornea. The creation of a refractive layer in a human cornea using methods described herein can be elected. For example, assuming a refractive index alteration of 1% in collagen tissue, the exposure of a layer of 50 μm thickness inside the anterior stroma of the cornea is sufficient to facilitate refractive corrections of up to +/−20 diopters. A series of modified loci layer is preferably positioned from 100 μm to 150 μm below the cornea surface. Corrections of toric and aspheric refractive errors, as well as higher order optical aberrations, can be achieved. The calculation of the required correction can be accomplished similarly to the case of customized IOL-design, by techniques well known in the art, or by the techniques described in my aforementioned copending application Ser. No. 12/717,866, The in situ tissue alteration process can be facilitated by the 2-photon microscope 704, providing online procedure control, based on autofluorescence imaging of the various cornea tissues.

In contrast to polymeric lens materials, the cornea tissue is not homogeneous. The structure of the cornea can be visualized by 2-photon microscopy, utilizing a fluorescence and second harmonic generation (SHG) imaging mode.

In FIG. 14, the creation of a refractive layer inside the anterior part of a human crystalline lens is depicted. Preferably, a layer 1410 is selected, which is positioned about 100 μm below the anterior lens capsule. The application for modifying lens tissue is especially suited for creating multifocalities in the presbyopic human eye to facilitate near vision or to correct myopia (nearsightedness) or hyperopia (farsightedness) and astigmatism (toricity).

It is believed the in situ modification of cornea and lens tissues can eventually substitute LASIK-surgery, refractive lens exchange (RLE) procedures, and Phakic lens procedures providing a non-invasive, patient-friendly alternative.

Although the present invention has been described in considerable detail with reference to the preferred versions thereof, other versions are possible. Therefore the scope of the appended claims should not be limited to the description of the preferred versions contained therein.

What is claimed is:

1. A method for modifying an optical property of a lens sized for placement in a human eye comprising the steps of:
  a) holding the lens external to an eye, the lens having an anterior surface, a posterior surface and an optical axis, and formed of an optical material having a first refractive index; and
  b) forming a contiguous three-dimensional patterned microstructure within a layer of the lens by modifying a plurality of contiguous loci in the layer by optically distributing a focused pulsed laser beam on each locus of said plurality of contiguous loci, causing a nonlinear absorption of photons by the optical material of each modified locus resulting in the optical material of the modified loci having a second refractive index that is different than the optical material before modification;
  wherein the contiguous three-dimensional patterned microstructure comprises a phase shifting optical structure that modifies the optical property of the lens, said phase shifting optical structure comprising a plurality of full-wave, phase-wrapped zones that compensate for optical path length differences within an array of neighboring light rays.

2. The method of claim 1, wherein the contiguous three-dimensional patterned microstructure formed in the forming step comprises a refractive structure.

3. The method of claim 1, wherein the layer is planar.

4. The method of claim 1, wherein the layer is substantially perpendicular to the optical axis.

5. The method of claim 1, wherein each modified locus is right cylindrically shaped and has an axis substantially parallel to the optical axis and an axial depth of at least 5 µm.

6. The method of claim 1, wherein the contiguous three-dimensional patterned microstructure comprises an annular ring pattern.

7. The method of claim 1 wherein the modified optical property comprises an adjustment of the diopter power of the lens by at least plus or minus 0.5.

8. The method of claim 1 wherein at least some of the loci modified during the forming step have an optical path length of from 0.1 to about 1 wavelength greater than the optical path length of a non-modified locus, wherein the wavelength is with respect to light of wavelength of 555 nm.

9. The method of claim 1 wherein at least some of the loci modified during the forming step are configured in a substantially circular pattern around the optical axis.

10. The method of claim 1 wherein sufficient loci are modified in the contiguous three-dimensional patterned microstructure during the forming step so that at least 90% of light projected onto the anterior surface in a direction generally parallel to the optical axis passes through at least one modified locus.

11. The method of claim 1 wherein both the posterior and anterior surfaces of the lens are substantially planar.

12. The method of claim 1 wherein each locus modified during the forming step has an axial depth of from 5 to 50 µm.

13. The method of claim 1 wherein the loci modified during the forming step have an axial depth varying from about 5 to 50 µm.

14. The method of claim 1 wherein each locus modified during the forming step has from 1 to 10 sites, the sites being arranged in an axial direction, each site being formed by a single burst of the focused laser beam.

15. The method of claim 1 wherein the phase shifting optical structure generates an aspherical focusing effect.

16. The method of claim 1 wherein the phase shifting optical structure generates a spherical focusing effect.

17. A method for modifying an optical property of a disc sized for use in a human eye, the disc having an anterior surface, a posterior surface and an optical axis, and formed of an optical material having a refractive index, the method comprising the step of:

forming a contiguous three-dimensional patterned microstructure within a layer of the disc by modifying the index of refraction of a plurality of contiguous loci in the layer of the disc while it is external to the eye by optically distributing a focused pulsed laser beam on each locus of said plurality of contiguous loci, causing nonlinear absorption of photons by the optical material of each modified locus, wherein the contiguous three-dimensional patterned microstructure comprises a phase shifting optical structure that modifies an optical property of the disc, said phase shifting optical structure comprising a plurality of full-wave, phase-wrapped zones that compensate for optical path length differences within an array of neighboring light rays.

18. The method of claim 17, wherein the contiguous three-dimensional patterned microstructure formed in the forming step comprises a refractive structure.

19. The method of claim 17, wherein the plurality of contiguous loci includes at least 1,000,000 modified loci in the layer.

20. The method of claim 17, wherein the layer is substantially perpendicular to the optical axis.

21. The method of claim 17, Wherein each modified locus is right cylindrically shaped and has an axis substantially parallel to the optical axis and an axial depth of at least 5 µm.

22. The method of claim 17, wherein the contiguous three-dimensional patterned microstructure formed in the forming step comprises an annular ring pattern.

23. The method of claim 17 wherein the layer is substantially parallel to the posterior surface.

24. The method of claim 17 wherein the layer is closer to the anterior surface than the posterior surface.

25. The method of claim 17 wherein the laser beam has a wavelength, and the disc comprises a polymeric matrix that includes an absorber for light of the laser beam wavelength.

26. The method of claim 17 wherein the disc includes an absorber of at least 0.01% by weight for light of the laser beam wavelength.

27. The method of claim 17 wherein the laser has a wavelength and the method further comprises selecting a disc formed of a polymeric matrix doped with an absorber for light of the laser beam's wavelength.

* * * * *